United States Patent
Lee et al.

(10) Patent No.: US 11,541,088 B2
(45) Date of Patent: Jan. 3, 2023

(54) COMPOSITION FOR PREVENTING, AMELIORATING OR TREATING SLEEP DISORDERS COMPRISING MEDICINAL HERB EXTRACT AS EFFECTIVE INGREDIENT

(71) Applicant: KOREA INSTITUTE OF ORIENTAL MEDICINE, Daejeon (KR)

(72) Inventors: Mi Young Lee, Seoul (KR); Yu Ri Kim, Daejeon (KR); Bo-Kyung Park, Daejeon (KR); Young Hwa Kim, Gyeonggi-do (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 171 days.

(21) Appl. No.: 17/058,861

(22) PCT Filed: May 23, 2019

(86) PCT No.: PCT/KR2019/006195
§ 371 (c)(1),
(2) Date: Nov. 25, 2020

(87) PCT Pub. No.: WO2019/225981
PCT Pub. Date: Nov. 28, 2019

(65) Prior Publication Data
US 2021/0145912 A1 May 20, 2021

(30) Foreign Application Priority Data
May 25, 2018 (KR) .......................... 10-2018-0059715

(51) Int. Cl.
*A61K 36/185* (2006.01)
*A23L 33/105* (2016.01)
*A61P 25/20* (2006.01)

(52) U.S. Cl.
CPC .......... *A61K 36/185* (2013.01); *A23L 33/105* (2016.08); *A61P 25/20* (2018.01); *A23V 2002/00* (2013.01); *A61K 2236/31* (2013.01); *A61K 2236/331* (2013.01); *A61K 2236/333* (2013.01)

(58) Field of Classification Search
None
See application file for complete search history.

(56) References Cited

U.S. PATENT DOCUMENTS
8,454,943 B2  6/2013  Florence et al.

FOREIGN PATENT DOCUMENTS

| CN | 105194490 A | 12/2015 |
| CN | 106360532 A | 2/2017 |
| JP | 2018-158891 A | 10/2018 |
| KR | 10-2007-0002718 A | 1/2007 |
| KR | 10-2012-0121938 A | 11/2012 |
| KR | 10-2017-0096586 A | 8/2017 |

OTHER PUBLICATIONS

Lee et al. (1999) Planta Medica 65: 658-660. (Year: 1999).*
Maganha et al. (2010) Food Chemistry 118: 1-10. (Year: 2010).*
Raskin et al. (2004) Current Pharmaceutical Design 10, 3419-3429. (Year: 2004).*
Revilla et al. (1998) J. Agric. Food Chem. 46: 4592-4597. (Year: 1998).*
International Search Report for PCT/KR2019/006195 dated Aug. 26, 2019.
Vanzella, C. et al. "Antidepressant-like effects of methanol extract of Hibiscus tiliaceus flowers in mice". BMC Complementary and Alternative Medicine, vol. 12(41). pp. 1-6, 2012.
Kim Hee-sung, "What you didn't know about Korea's national flower", Korea net: The official website of the Republic of Korea, 2019.

* cited by examiner

*Primary Examiner* — Russell G Fiebig
(74) *Attorney, Agent, or Firm* — The PL Law Group, PLLC

(57) ABSTRACT

A method for treating a sleep disorder according to an embodiment of the present disclosure includes administering a composition comprising an extract of *Hibiscus syriacus* as an effective ingredient to a subject in need thereof. Because the *Hibiscus syriacus* extract of the present invention has an effect of improving sleep time deteriorated by stress, and an effect of reducing the content of corticosterone, which increases due to stress, and increasing the content of serotonin in blood. In addition, the composition has an effect of enhancing in a significant sense the expression of GABAR A α1 in cerebral cortex, which decreases due to stress, in a group administered with *Hibiscus syriacus* extract. As such, the composition comprising *Hibiscus syriacus* extract as an effective ingredient as an effective ingredient can be advantageously used as a functional health food composition or a pharmaceutical composition for preventing, ameliorating or treating sleeping disorders.

5 Claims, 4 Drawing Sheets

COMPOSITION FOR PREVENTING, AMELIORATING OR TREATING SLEEP DISORDERS COMPRISING MEDICINAL HERB EXTRACT AS EFFECTIVE INGREDIENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/006195, filed May 23, 2019, which claims priority to the benefit of Korean Patent Application No. 10-2018-0059715 filed in the Korean Intellectual Property Office on May 25, 2018, the entire contents of which are incorporated herein by reference.

TECHNICAL FIELD

The present invention relates to a composition for preventing, ameliorating or treating sleep disorders comprising medicinal herb extract as an effective ingredient.

BACKGROUND ART

Sleep is a state in which conscious activity is in rest with eyes closed, and it is an important process of restoring the energy consumed during daytime activity and recovering from the fatigue accumulated through physical activities. Sleep is not only a period during which energy restoration and fatigue recovery occur but also a period during which the growth hormone that is essentially required for human growth are secreted in the largest amount.

In human body, the brain governs all physiological functions for sustaining life and, for maintaining a suitably balanced activity, the brain needs a rest, which is mostly achieved during sleep. Due to the overwhelming and busy daily cycle of modern life, increased prevalence in obesity, population aging, and the like, the number of patients who are treated after diagnosis with sleep disorders has increased in last several years. The number is expected to continue to rise in the coming years.

Among the various types of sleep disorders, insomnia is one of the most common sleep disorders and it is defined as a symptom of having difficulty with sleep like difficulty to fall asleep, difficulty to maintain sleep, shallow sleep, or poor sleep quality. Regardless of the stage of insomnia, it is reported that three in ten adults suffer from sleep disorders and the ratio is even higher in women and seniors.

The reason of having drastically reduced sleep duration by people in the modern world is based on various causes like an increase in mental disorders that are based on psychological reasons such as anxiety about future, depression, anxiety disorder, or stress, alternating day and night shifts resulting from diversity in jobs and society, unhealthy lifestyles, and the like. Namely, the more complex society becomes, the more jobs to be done and the more stress to be dealt with, yielding chronic sleep deficiency. In addition, drinking excess amounts of caffeinated beverages like coffee is also considered to be one reason of having sleep deficiency. Temporary acute insomnia easily occurs due to the irregular sleeping habit caused by temporary stress, change in sleeping habit, or the like. Temporary acute insomnia can be overcome when regular sleeping habit is practiced and underlying issues or stress for causing insomnia are removed so that normal sleeping habit can be restored. However, if a person continues to have a bad sleeping habit or deals with the insomnia in wrongful way, chronic insomnia in which he or she has trouble falling and/or staying asleep every night is caused. Symptoms of chronic insomnia impair the quality of life and increase a risk for depression by 10 times of more. In addition, sleep disorders caused by insomnia increase the prevalence of various diseases by causing problems in controlling high blood pressure, blood sugar level, obesity or the like, and they also exhibit an influence on social aspect of a patient including higher medical cost, increased risk of having accidents during daytime, poor performance at work, or the like.

Meanwhile, *Hibiscus syriacus* is the other name of rose of Sharon (*Hibiscus syriacus* L.), and as a herbal medicine name, *Hibiscus syriacus* skin, *Hibiscus syriacus* flower, *Hibiscus syriacus* root, and *Hibiscus syriacus* seed are used. Rose of Sharon is a deciduous tree belonging to Malvaceae family, and, in South Korea, it is found a region below Pyeongnam province and Kangwon province. According to the Korean Herbal Pharmacopoeia (Herbal Medicine), skins of stems and roots of rose of Sharon are defined as hibisci cortex. According to the descriptions of Donguibogam (i.e., a classic book on Korean traditional medicine), it is described as follows: "[I]t has a mild pharmaceutical property without any toxicity, can stop chronic furuncle and bleeding, is effective for thirstiness after diarrhea, and can promote sleeping. The flower has a cold pharmaceutical property without any toxicity, is useful for treating red dysentery and white dysentery, and taken after roasting or as a tea for treating chronic furuncle and bleeding." According to the description of Bonchogangmok (i.e., another classic book on Korean traditional medicine), it is useful for treating red leucorrhea or white leucorrhea of women, stopping pains associated with abscess, yielding clear eyes when washed with water boiled with plant as an agent for treating scabies, and also promoting blood circulation.

As a technique relating to treat sleep disorders using *Hibiscus syriacus* that is known to date, it is described in Chinese Patent Publication No. 106360532 that mum flower sauce containing petal and flow extract of rose of Sharon is effective for treating insomnia. In Chinese Patent Publication No. 105194490, it is described that a mixture containing 16 kinds of medicinal herbs in addition to *Hibiscus syriacus* skin has an effect of treating insomnia. However, so far there is no disclosure of a composition for preventing, ameliorating or treating sleep disorders comprising medicinal herb extract as an effective ingredient as it is disclosed in the present invention.

SUMMARY

The present invention is devised under the circumstances described above. The present invention relates to a composition for preventing, ameliorating or treating sleep disorders comprising medicinal herb extract as an effective ingredient. Specifically, by finding that *Hibiscus syriacus* extract, which is a medicinal herb extract contained as an effective ingredient, has an effect of improving the quality of sleep deteriorated by stress, an effect of reducing the content of corticosterone and increasing the content of serotonin in blood, and also an effect of enhancing the expression of GABAR (GABA receptor) A $\alpha 1$ in cerebral cortex, the present invention is completed.

To achieve the purpose described above, the present invention provides a functional health food composition for preventing or ameliorating sleep disorders comprising an extract of *Hibiscus syriacus* as an effective ingredient.

The present invention further provides a pharmaceutical composition for preventing or treating sleep disorders comprising an extract of *Hibiscus syriacus* as an effective ingredient.

The present invention relates to a composition for preventing, ameliorating or treating sleep disorders comprising medicinal herb extract as an effective ingredient. Specifically, it is shown that the composition has an effect of ameliorating sleep disorders by increasing REM (rapid eye movement) and NonREM (non-rapid eye movement) sleep in addition to reducing the wake in an animal model which has a sleep disorder due to stress, and also an effect of reducing the content of corticosterone in blood which is increased by stress and increasing the content of serotonin. Furthermore, in a group administered with *Hibiscus syriacus* extract, there is an effect of enhancing in a significant sense the expression of GABAR A α1, which is reduced in cerebral cortex due to stress.

DETAILED DESCRIPTION

Figure 1:
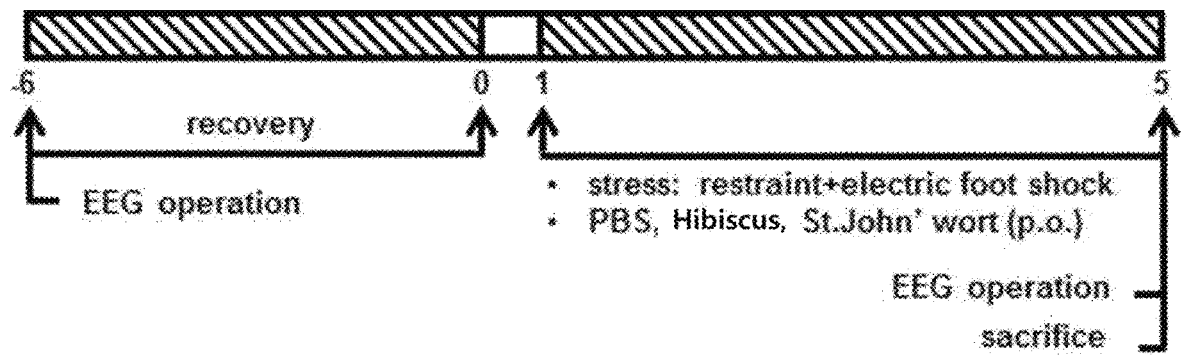
FIG. 1 is a diagram illustrating the process of carrying out a stress-caused sleep disorder test.

The present invention relates to a functional health food composition for preventing or ameliorating sleep disorders comprising *Hibiscus syriacus* extract as an effective ingredient.

A solvent for extracting the *Hibiscus syriacus* extract is preferably at least one selected from water, $C_1$-$C_4$ lower alcohol, acetone, ethyl acetate, butyl acetate, 1,3-butylene glycol, and hexane. It is more preferable to use water, $C_1$-$C_4$ lower alcohol, or a mixture thereof, and even more preferable to use ethanol, but it is not limited thereto.

With regard to a method for preparing the *Hibiscus syriacus* extract of the present invention, any kind of common methods that are generally known as an extraction method in the pertinent art, e.g., filtration, hot water extraction, impregnation extraction, extraction by reflux condensation, and ultrasonic extraction, can be used. It is preferable that the extraction is carried out by adding an extraction solvent in an amount of 2 to 40 times the volume of dried *Hibiscus syriacus*. The extraction temperature is preferably between 20° C. and 100° C., and most preferably 80° C. and 95° C., but it is not limited thereto. Furthermore, the extraction time is preferably between 0.5 hour and 10 hours, more preferably between 1 hour and 4 hours, and most preferably 3 hours, but it is not limited thereto. Concentration is preferably concentration under reduced pressure which uses a vacuum condenser or a vacuum rotary evaporator, but it is not limited thereto. Furthermore, the drying is preferably carried out by drying under reduced pressure, drying under vacuum, drying under boiling, spray drying, or freeze drying, but it is not limited thereto.

The *Hibiscus syriacus* extract can be extracted by using whole plant or specific part (skin, root, flower, or the like) of *Hibiscus syriacus*. The extract is preferably extracted from a flower of *Hibiscus syriacus*, but it is not limited thereto.

The sleep disorders are preferably insomnia caused by stress, but it is not limited thereto.

The functional health food composition of the present invention comprising *Hibiscus syriacus* extract as an effective ingredient may be directly added to a food product or used with other food product or food ingredient, and it can be suitably used according to a common method. The mixing amount of the effective ingredient can be suitably determined based on the purpose of use (i.e., prevention or amelioration). In general, the amount of *Hibiscus syriacus* extract to be comprised in the functional health food composition can be 0.1 to 90 parts by weight relative to the total weight of the functional health food composition. However, in case of long-term consumption under the purpose of maintaining good health and hygiene or managing health, it can be an amount below the aforementioned range, and, as there is no problem in terms of safety, the effective ingredient may be also used in an amount above the aforementioned range.

When the functional health food composition of the present invention is consumed in the form of a beverage, other ingredients are not particularly limited except that, as an essential ingredient, the aforementioned extract of *Hibiscus syriacus* is comprised at indicated ratio, and, like common beverages, various flavors or natural carbohydrates can be comprised as an additional component. Examples of the natural carbohydrates include monosaccharides such as glucose or fructose, disaccharides such as maltose or sucrose, polysaccharides such as dextrin or cyclodextrin, and sugar alcohols such as xylitol, sorbitol, or erythritol. As a flavor other than those described above, natural flavor (thaumatin, *stevia* extract (e.g., rebaudioside A and glycyrrhizin)) and synthetic flavor (e.g., saccharine and aspartame) can be advantageously used.

The functional health food composition of the present invention may further comprise, other than the effective ingredient, at least one selected from a nutritional supplement, a vitamin, an electrolyte, a flavor, a coloring agent, an enhancing agent, pectinic acid and a salt thereof, alginic acid and a salt thereof, an organic acid, protective colloidal thickening agent, a pH adjusting agent, a stabilizer, a preservative, glycerin, alcohol, and a carbonating agent used for carbonated drink. Other than those, fruit flesh for producing natural fruit juice or vegetable drink can be comprised in the functional health food composition of the present invention. The fruit flesh may be used either independently or in combination thereof. Ratio of the above various additives is not critical, but it is generally selected from a range of about 0.1 to 20 parts by weight relative to 100 parts by weight of the *Hibiscus syriacus* extract of the present invention.

The functional health food composition of the present invention is preferably produced in any one formulation selected from a powder, a granule, a pill, a tablet, a capsule, a candy, a syrup, and a drink, but it is not limited thereto.

The present invention further provides a pharmaceutical composition for preventing or treating sleep disorders comprising an extract of *Hibiscus syriacus* as an effective ingredient.

The pharmaceutical composition of the present invention may further comprise a carrier, vehicle, or diluent, and can be prepared in various formulations including an oral formulation and a parenteral formulation. In case of producing a formulation, production is made by using a diluent or a vehicle such as filler, bulking agent, binding agent, moisturizing agent, disintegrating agent, or surfactant that are commonly used for producing a formulation, but it is not limited thereto.

As for the solid formulation for oral administration, a tablet, a pill, a powder, a granule, a capsule or the like are included, and such solid formulation is produced by mixing at least one compound with one or more vehicles such as starch, calcium carbonate, sucrose, lactose, or gelatin. Furthermore, other than simple vehicles, a lubricating agent such as magnesium stearate or talc can be also used. As for the liquid formulation for oral administration, a suspension, an emulsion, a syrup formulation, or the like can be mentioned. Other than water or liquid paraffin as a commonly used simple diluent, various kinds of a vehicle such as moisturizing agent, sweetening agent, aromatic agent, or preservatives may be included.

Examples of a formulation for parenteral administration include a sterilized aqueous solution, a non-aqueous formulation, a suspension, an emulsion, a freeze-dried formulation, and a suppository. As a water insoluble solvent or a suspending agent, propylene glycol, polyethylene glycol, or vegetable oil such as olive oil, and injectable ester such as ethylolate can be used. As a base for a suppository, witepsol, macrogol, tween 61, cacao fat, laurin fat, glycerol, gelatin, or the like can be used.

The pharmaceutical composition of the present invention can be administered either orally or parenterally. In case of parenteral administration, it is preferable to choose external application on skin, intraperitoneal, rectal, intravenous, muscular, subcutaneous, endometrium injection, or intracerebroventricular injection, but it is not limited thereto.

The pharmaceutical composition of the present invention is administered in a pharmaceutically effective amount. As described herein, the expression "pharmaceutically effective amount" means an amount sufficient for treating a disorder at reasonable benefit-risk ratio that can be applied for a medical treatment. The effective dose level may be determined based on a type or severeness of a disorder, activity of a pharmaceutical, sensitivity to a pharmaceutical, administration period, administration route, excretion ratio, time period for therapy, elements including a pharmaceutical used in combination, and other elements that are well known in the medical field. The composition of the present invention can be administered as a separate therapeutic agent, or it can be used in combination with other therapeutic agent. It can be administered in order or simultaneously with a conventional therapeutic agent. It can be also administered as single-dose or multi-dose. It is important to administer an amount which allows obtainment of the maximum effect with minimum dose while considering all of the aforementioned elements without having any side effect, and the dosage can be easily determined by a person skilled in the pertinent art.

The dosage of the composition of the present invention may vary depending on bodyweight, age, sex, health state, diet of a patient, administration period, administration method, excretion rate, and severeness of disorder. However, the daily dosage is, in terms of the amount of an extract of *Hibiscus syriacus*, 0.01 to 1,000 mg/kg, preferably 30 to 500 mg/kg, and more preferably 50 to 300 mg/kg, and it can be administered 1 to 6 times per day. However, since the dosage may be increased or decreased depending on the administration route, severeness of obesity, sex, body weight, age or the like, the scope of the present invention is not limited by the aforementioned dosage in any sense.

Hereinbelow, the present invention is explained in greater detail in view of the Examples. However, the following Examples are given only for specific explanation of the present invention and it would be evident to a person who has common knowledge in the pertinent art that the scope of the present invention is not limited by them.

Examples

<Methods>
1. Production and Preparation of Sample

Hibiscus syriacus petals were added to 30% (v/v) ethanol solution (10 to 15 times the volume of Hibiscus syriacus) and subjected to distillation extraction for 3 hours. The extracted solvent was concentrated by a first filtering using a filter net and a second filtering using cotton, and then prepared in powder form by lyophilization.

2. Administration of Test Material and Classification of Test Group

Thirty minutes before application of stress, the chemical was orally administered in an amount of 0.1 ml while the solvent (0.1 ml) was orally administered to the normal group and the stress control group. The test was carried out for total 6 groups [i.e., normal, control (stress), positive control (PC, St. John's wort), Hibiscus syriacus extract (50, 100, or 200 mg/kg)] in which 6 animals were used for each group, i.e., total 36 animals were used.

3. Operation for Electroencephalography (EEG)

A male rat (7 week old) was suitably fed with solid feed and water till the test day. After the acclimation for 1 week in an environment in which temperature of 23 to 25° C., humidity of 45 to 60%, and illuminance of 200 to 300 LUX, and 12 hour light and dark cycle are maintained, the animals were subjected to the test. For the operation, a 7-week old SD (Sprague Dawley) rat was anesthetized by intraperitoneal injection of 40 mg/kg pentobarbital, and then placed and fixed on a stereotaxic instrument (Stoelting CO, USA) such that the bregma and lambda are in horizontal alignment. After suppressing subgaleal bleeding, hairs were shaved and the skull was exposed by excising the scalp and removing the periosteum. Based on the anatomy drawing by Paxinos & Watson, a hole was created by using drill, an electrode was inserted to reach the dura mater, and an electrode composed of two silver wires was inserted to neck muscle to record an electromyogram. On top of the cranial bone of cerebellum, pins attached with an electrode for recording an electroencephalogram and an electrode for recording an electromyogram were placed and fixed on top of the cranial bone by applying dental cement. Rat after the operation was placed in a cage in a breeding room, one rat per cage, and then allowed to recover for one week.

4. Animal Model with Sleep Disorder Induced by Stress

After the recovery from the operation, the test was carried out as summarized in FIG. 1. A foot pad electric shock stress test was then carried out every day for 5 days in total. To induce a sleep disorder, an electric shock at strength of 1 mA was randomly applied for 5 minutes (10 times per 3 seconds) to a foot pad of the rat.

5. Electroencephalography (EEG) Measurement

After the stress for 5 days, the rat was orally administered with each pharmaceutical, and, after 30 minutes, EEG recording was carried out in a light-blocking acrylic cylinder (PM 8:00 to AM 8:00). The wake time and sleep (REM and Non-REM) time were recorded by using SleepSign Ver. 3 Software (Kissei Comtec, Nagano, Japan), which is a professional program for analyzing animal sleep.

6. Measurement of Corticosterone in Blood Serum

Upon the completion of the test, blood serum was separated from each animal and corticosterone content in separated blood serum was measured. First, according to the manual of corticosterone ELISA Kit (Cayman Chemical Company, Ann Arbor, Mich., USA), ELISA buffer solution was added in an amount of 100 µl to a non-specific binding well of goat anti-mouse IgG coated microplate. To a $B_0$ well, 50 µl of ELISA buffer solution was added. To the standard and sample wells, each of the prepared test materials was added in an amount of 50 µl, and then diluted corticosterone AChE tracer was added in an amount of 50 µl to all wells except the blank well and the total activity well. Except the blank well, total activity well, and non-specific binding well, diluted corticosterone ELISA anti blood serum (50 µl) was added. After the overnight reaction at 4° C. followed by washing 5 times, each well was reacted with diluted Ellman's reagent (200 µl) while Ellman's Reagent was added in an amount of 5 µl to the total activity well to adjust the total amount. After the shaking and reaction for 90 to 120 minutes using an orbital shaker, absorbance at a wavelength of 405 nm was measured.

7. Measurement of Serotonin in Blood Serum

Upon the completion of the test, blood serum was separated from each animal and serotonin content in separated blood serum was measured. First, according to the manual of serotonin ELISA kit (Abcam Inc, Cambridge, UK), the analysis buffer was added in an amount of 150 µl to a non-specific binding well of goat anti-rabbit IgG microplate. To a $B_0$ well, 100 µl of the analysis buffer was added. Each of the standard and sample wells was added with 100 µl of the analysis buffer, and then the serotonin alkaline phosphatase conjugate was added in an amount of 50 µl except the total activity well and the blank well. Except the blank well, total activity well, and non-specific binding well, serotonin antibody was added to $B_0$, the standard, and the test group. After shaking for 2 hours at 500 rpm at room temperature followed by washing 3 times, the serotonin alkaline phosphatase conjugate (20× diluted) was added in an amount of 5 µl only to the total activity well. Finally, pNpp substrate solution was added in an amount of 200 µl for each, and then the reaction was allowed to occur for 1 hour at room temperature without shaking. After terminating the chromogenic reaction using termination solution (50 µl), the reaction was terminated and absorbance at a wavelength of 405 nm was measured.

8. Western Blot

Extracted cerebral cortex tissues were added to a lysis buffer (300 µl) followed by homogenization. By carrying out centrifuge for 20 minutes at 13,000 rpm, a lysate was obtained. The resulting lysate was separated on a SDS-PAGE gel and transferred onto a membrane followed by blocking. Then, it was reacted with GABAR A α1 antibody for 16 hours at 4° C. Reaction with HRP-linked secondary antibody was allowed to occur for 1 hour at room temperature, and the analysis was made by development using LAS-3000 image analyzer (Fuji Photo Film Co., Tokyo, Japan).

9. Statistical Treatment

The results are given in mean±standard deviation, and the statistical comparison among test groups was achieved by carrying out one-way measures analysis of variance (ANONA) based on Tukey's Honest Significant Difference (HSD). $p<0.05$ was taken to have statistical significance.

Example 1. Determination of Effect of Hibiscus syriacus Extract on Wake Time During Sleep of SD Rat which has Sleep Disorder Induced by Stress To determine the effect of Hibiscus syriacus extract on wake time during sleep of SD rat which has a sleep disorder according to application of stress, via oral administration according to the aforementioned test method, the normal group not applied with any stress and stress control group were administered with a solvent while the positive control group was administered with 200 mg/kg St. John's wort extract and the *Hibiscus syriacus* extract administration group of the present invention was administered with 50, 100, or 200 mg/kg *Hibiscus syriacus* extract.

Thirty minutes after the oral administration of a substance belonging to each group for five days, foot pad electric shock was applied to the SD rat except the normal group to induce a sleep disorder caused by stress. Wake time was measured for each rat.

Figure 2:
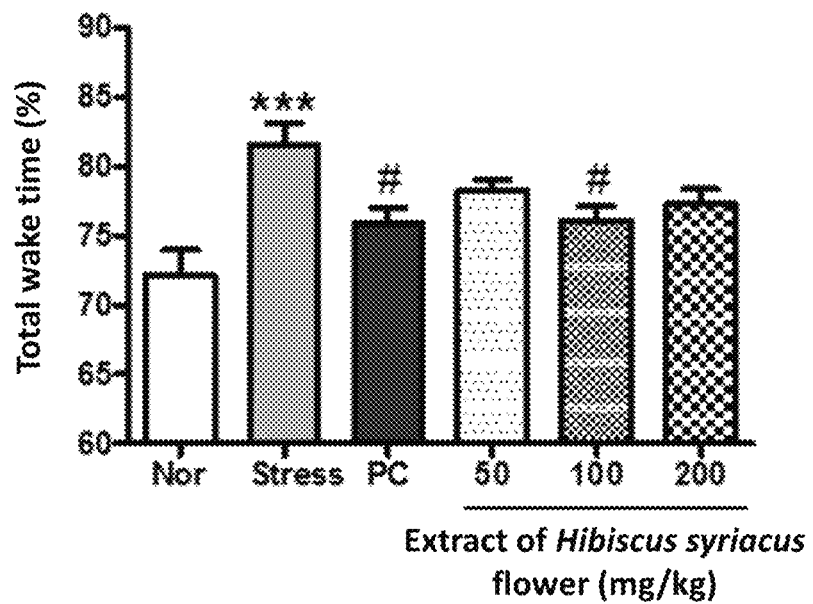
FIG. 2 shows the result of measuring the wake time by determining EEG after administering for 5 days the extract of *Hibiscus syriacus* flower (50, 100 or 200 mg/kg) or St. John's wort (200 mg/kg) as a positive control (PC) to a SD rat with sleep disorder which is induced by electric shock stress applied on foot pad. *** indicates that, compared to the normal group (Nor), the wake time has increased in a statistically significant sense in the stress group (Stress) ($p<0.001$). # indicates that, compared to the stress group, the wake time has decreased in a significant sense in the test group administered with the extract of *Hibiscus syriacus* flower of the present invention ($p<0.05$).

As the result is shown in FIG. 2, the wake time during sleep has increased in a statistically significant sense in the stress control group compared to the normal group while it has decreased in the group administered with *Hibiscus syriacus* extract or St. John's wort compared to the stress control group. From the group administered with 100 mg/kg *Hibiscus syriacus* extract, a decrease in a statistically significant sense was shown.

Example 2. Determination of Effect of *Hibiscus syriacus* Extract on REM Time During Sleep of SD Rat which has Sleep Disorder Induced by Stress To determine the effect of *Hibiscus syriacus* extract on REM time during sleep of SD rat which has a sleep disorder according to application of stress, via oral administration according to the aforementioned test method, the normal group not applied with any stress and stress control group were administered with a solvent while the positive control group was administered with 200 mg/kg St. John's wort extract and the *Hibiscus syriacus* extract administration group of the present invention was administered with 50, 100, or 200 mg/kg *Hibiscus syriacus* extract.

Thirty minutes after the oral administration of a substance belonging to each group for five days, foot pad electric shock was applied to the SD rat except the normal group to induce a sleep disorder caused by stress. REM time was measured for each rat.

Figure 3:
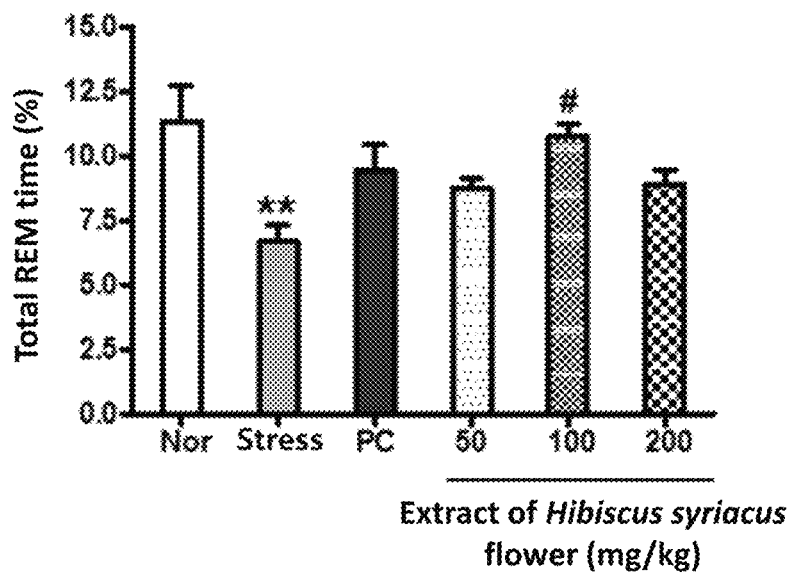
FIG. 3 shows the result of measuring the REM sleep time by determining EEG after administering for 5 days the extract of *Hibiscus syriacus* flower (50, 100 or 200 mg/kg) or St. John's wort (200 mg/kg) as a positive control (PC) to a SD rat with sleep disorder which is induced by electric shock stress applied on foot pad. ** indicates that, compared to the normal group (Nor), the REM time has decreased in a statistically significant sense in the stress group (Stress) ($p<0.01$). # indicates that, compared to the stress group, the REM time has increased in a statistically significant sense in the test group administered with the extract of *Hibiscus syriacus* flower of the present invention ($p<0.05$).

As the result is shown in FIG. 3, the REM time during sleep has decreased in a statistically significant sense in the stress control group compared to the normal group while it has increased in the group administered with *Hibiscus syriacus* extract or St. John's wort compared to the stress control group. From the group administered with 100 mg/kg *Hibiscus syriacus* extract, an increase in a statistically significant sense was shown.

Example 3. Determination of Effect of *Hibiscus syriacus* Extract on NonREM Time During Sleep of SD Rat which has Sleep Disorder Induced by Stress To determine the effect of *Hibiscus syriacus* extract on NonREM time during sleep of SD rat which has a sleep disorder according to application of stress, via oral administration according to the aforementioned test method, the normal group not applied with any stress and stress control group were administered with a solvent while the positive control group was administered with 200 mg/kg St. John's wort extract and the *Hibiscus syriacus* extract administration group of the present invention was administered with 50, 100, or 200 mg/kg *Hibiscus syriacus* extract.

Thirty minutes after the oral administration of a substance belonging to each group for five days, foot pad electric shock was applied to the SD rat except the normal group to induce a sleep disorder caused by stress. NonREM time was measured for each rat.

Figure 4:
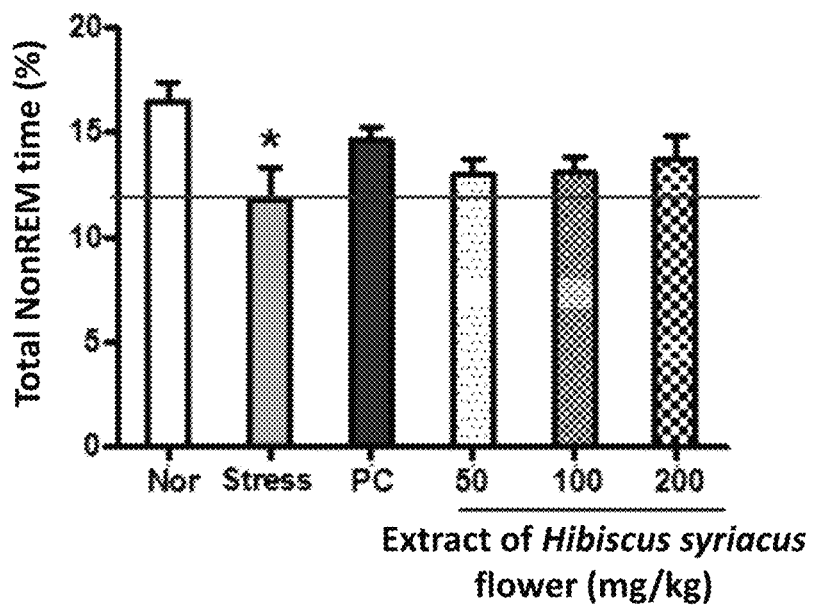
FIG. 4 shows the result of measuring the NonREM sleep time by determining EEG after administering for 5 days the extract of *Hibiscus syriacus* flower (50, 100 or 200 mg/kg) or St. John's wort (200 mg/kg) as a positive control (PC) to a SD rat with sleep disorder which is induced by electric shock stress applied on foot pad. * indicates that, compared to the normal group (Nor), the NonREM time has decreased in a statistically significant sense in the stress group (Stress) ($p<0.05$).

As the result is shown in FIG. 4, the NonREM time during sleep has decreased in a statistically significant sense in the stress control group compared to the normal group while it has increased in the group administered with *Hibiscus syriacus* extract or St. John's wort compared to the stress control group.

Example 4. Effect of *Hibiscus syriacus* Extract on Blood Corticosterone of SD Rat which has Sleep Disorder Induced by Stress To determine the effect of *Hibiscus syriacus* extract on blood corticosterone level of SD rat with induced sleep disorder, test materials were administered for 5 days according to the aforementioned test method. After collecting blood from the stressed rat by autopsy, the blood was centrifuged and content of corticosterone in blood serum was measured by ELISA.

Figure 5:
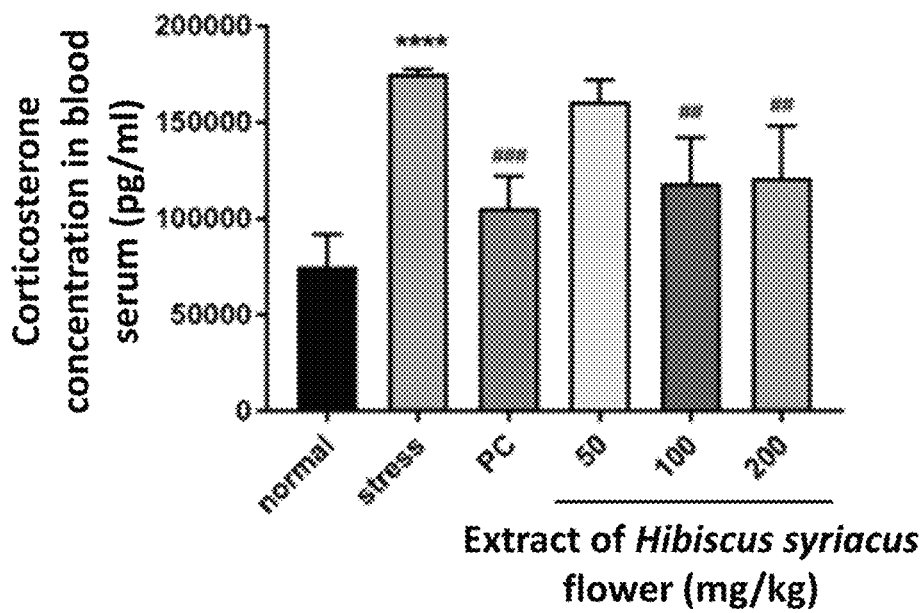
FIG. 5 shows the result of measuring, by enzyme linked immunosorbent assay (ELISA), the content of corticosterone in blood after administering for 5 days the extract of *Hibiscus syriacus* flower (50, 100 or 200 mg/kg) or St. John's wort (200 mg/kg) as a positive control (PC) to a SD rat with sleep disorder which is induced by electric shock stress applied on foot pad. **** indicates that, compared to the normal group (normal), the corticosterone content has increased in a statistically significant sense in the stress group (Stress) ($p<0.0001$). ## and ### indicate that, compared to the stress group, the corticosterone content in blood has decreased in a statistically significant sense in the positive control group and also in the test group administered with the extract of *Hibiscus syriacus* flower of the present invention (##; $p<0.01$, ###; $p<0.001$).

As the result is shown in FIG. 5, the content of corticosterone has decreased in a significant sense in the group administered with *Hibiscus syriacus* extract compared to the stress control group.

Example 5. Effect of *Hibiscus syriacus* Extract on Blood Serotonin of SD Rat which has Sleep Disorder Induced by Stress To determine the effect of *Hibiscus syriacus* extract on blood serotonin concentration of SD rat with induced sleep disorder, test materials were administered for 5 days according to the aforementioned test method. After collecting blood from the stressed rat by autopsy, the blood was centrifuged and content of serotonin in blood serum was measured by ELISA.

Figure 6:
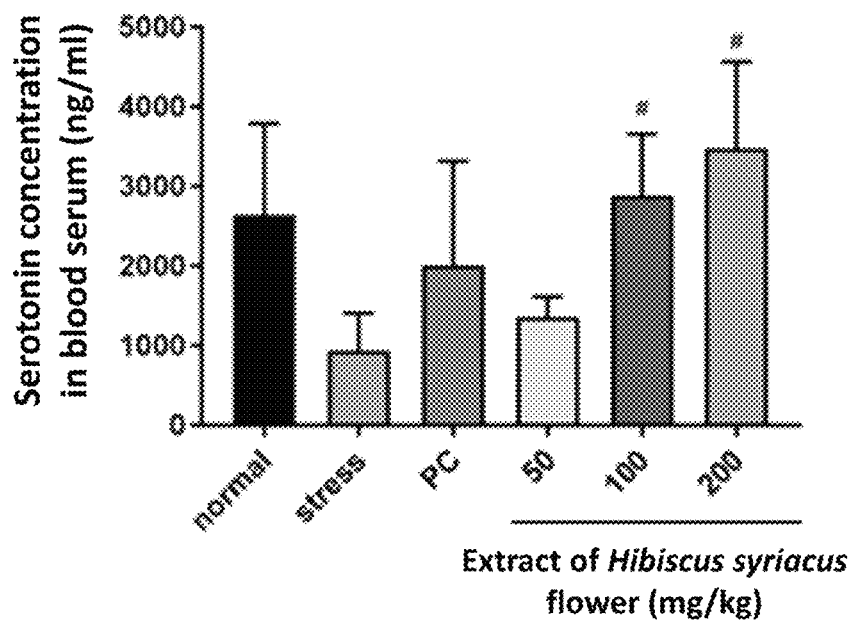
FIG. 6 shows the result of measuring, by ELISA, the content of serotonin in blood after administering for 5 days the extract of *Hibiscus syriacus* flower (50, 100 or 200 mg/kg) or St. John's wort (200 mg/kg) as a positive control (PC) to a SD rat with sleep disorder which is induced by electric shock stress applied on foot pad. # indicates that, compared to the stress group, the serotonin content in blood has increased in a statistically significant sense in the test group administered with the extract of *Hibiscus syriacus* flower of the present invention ($p<0.05$).

As the result is shown in FIG. 6, the content of serotonin has increased in a significant sense in the group administered with *Hibiscus syriacus* extract compared to the stress control group.

Figure 7:
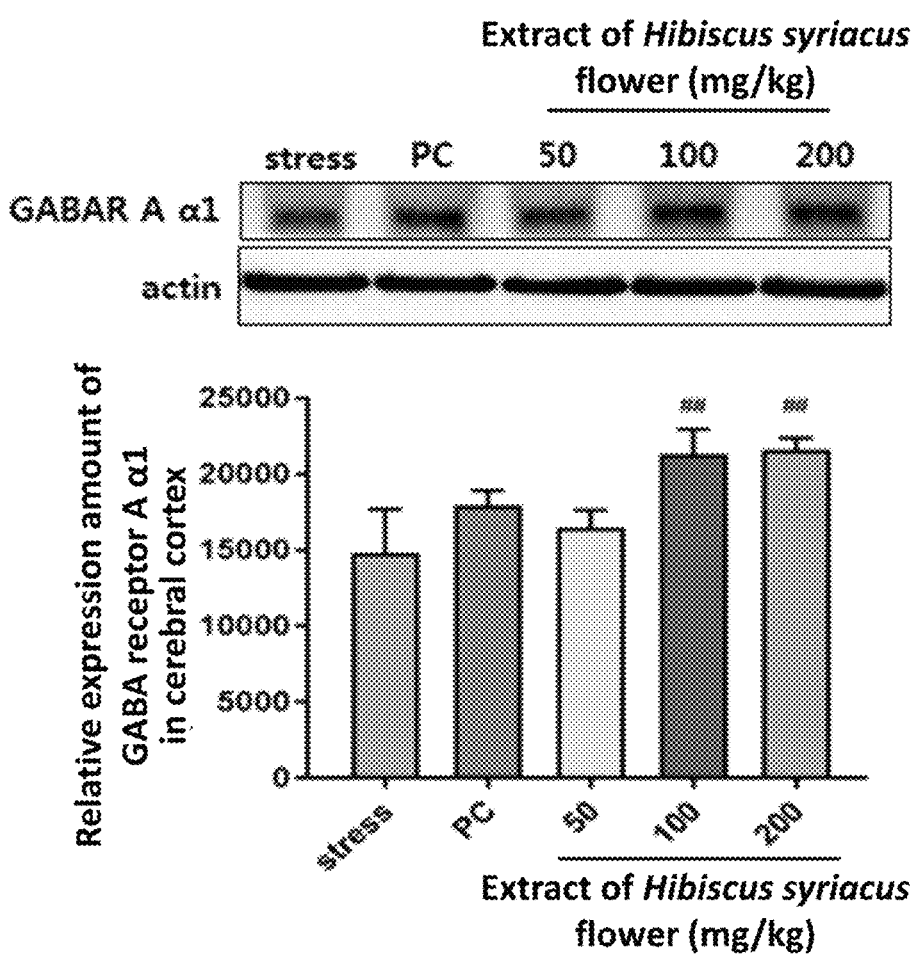
FIG. 7 shows the result of measuring, by a protein detection test, the expression amount of GABAR A α1 in cerebral cortex after administering for 5 days the extract of *Hibiscus syriacus* flower (50, 100 or 200 mg/kg) or St. John's wort (200 mg/kg) as a positive control (PC) to a SD rat with sleep disorder which is induced by electric shock stress applied on foot pad. ## indicates that, compared to the stress group, the expression amount of GABAR A α1 in cerebral cortex has increased in a statistically significant sense in the test group administered with the extract of *Hibiscus syriacus* flower of the present invention ($p<0.01$).

Example 6. Effect of *Hibiscus syriacus* Extract on Expression of GABAR A α1 in Cerebral Cortex of SD Rat which has Sleep Disorder Induced by Stress To determine the effect of *Hibiscus syriacus* extract on expression of GABAR A α1 in cerebral cortex of SD rat with induced sleep disorder, test materials were administered for 5 days according to the aforementioned test method. After collecting cerebral cortex from the stressed rat by autopsy, the cerebral cortex was centrifuged with buffer solution and the expression amount of GABAR A α1 in lysate was measured by a protein detection method As the result is shown in FIG. 7, the expression of GABAR A α1 has increased in a significant sense in the group administered with *Hibiscus syriacus* extract compared to the stress control group.

What is claimed is:
1. A method for treating insomnia, the method comprising:
  administering a composition comprising an extract of *Hibiscus syriacus* flower as an effective ingredient to a subject in need thereof,
  wherein the extract of *Hibiscus syriacus* flower is an extract extracted with an ethanol solution;

the insomnia is caused by an increased wake and a reduced REM (Rapid eye movement) sleep and Non-REM (Non-Rapid eye movement) sleep during sleeping; and the extract of *Hibiscus syriacus* flower reduces wake and increases REM (Rapid eye movement) sleep and Non-REM (Non-Rapid eye movement) sleep during sleeping to improve sleep quality.

2. The method of claim 1, wherein the composition is in a formulation selected from the group consisting of a powder, a granule, a pill, a tablet, a capsule, a candy, a syrup, and a drink.

3. The method of claim 1, wherein the composition is included in a health food.

4. The method of claim 1, wherein the composition is a pharmaceutical composition.

5. The method of claim 4, wherein the pharmaceutical composition further comprises at least one of a pharmaceutically acceptable carrier, a pharmaceutically acceptable vehicle, or a diluent.

* * * * *